United States Patent [19]

Oroszlan et al.

[11] Patent Number: 5,668,149
[45] Date of Patent: Sep. 16, 1997

[54] INHIBITION OF HUMAN IMMUNODEFICIENCY VIRUS-1 INFECTIVITY IN HUMAN CELLS

[75] Inventors: Stephen Oroszlan, Potomac; Wen-Po Tsai, Walkersville; Peter L. Nara, Frederick; Hsiang-Fu Kung, Middletown, all of Md.

[73] Assignee: The United States of America as represented by the Department of Health and Human Services, Washington, D.C.

[21] Appl. No.: 470,692

[22] Filed: Jan. 26, 1990

[51] Int. Cl.$^6$ .................................................. A61K 31/47
[52] U.S. Cl. ........................................................... 514/313
[58] Field of Search ............................................. 514/313

[56] References Cited

U.S. PATENT DOCUMENTS 5,153,202  10/1992  Davis ........................................ 514/311

FOREIGN PATENT DOCUMENTS

WO 9000055  1/1990  WIPO .

OTHER PUBLICATIONS

B.S. Stein et al, Cell, vol. 49, pp. 659–668, Jun. 5, 1987.
Stedman's Medical Dictionary, 23rd Edition, pp. 461 and 495.
Kagan, West J. Med, 146 (2), p. 234, Feb., 1987.
Chemical Abstracts 113: 536f (1990) Abstracting PCT Int. Application WO 90 00,055 Jan. 11, 1990.

*Primary Examiner*—Jerome D. Goldberg
*Attorney, Agent, or Firm*—Birch, Stewart, Kolasch & Birch, LLP

[57] ABSTRACT

Methods are disclosed for inhibiting the infectivity of HIV-1 in human cells. The methods comprise contacting human cells infected with HIV-1, with certain quinolinyl and acridinyl derivatives, including amodiaquin, chloroquine, hydroxychloroquine, primoquine, quinacrine and compounds having the formula:

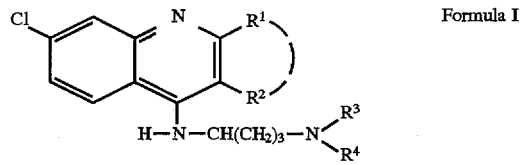

Formula I wherein $R^1$ and $R^2$ are each hydrogen, or join to form a cyclic structure of the formula:

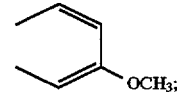

and $R^3$ and $R^4$, same or different, are hydrogen, $C_1$–$C_8$ lower alkyl or hydroxy substituted $C_1$–$C_8$ lower alkyl, and the pharmaceutically acceptable salts thereof.

4 Claims, 2 Drawing Sheets

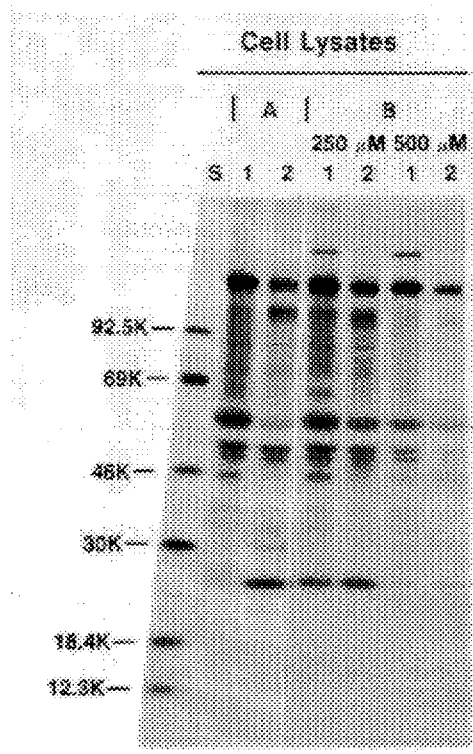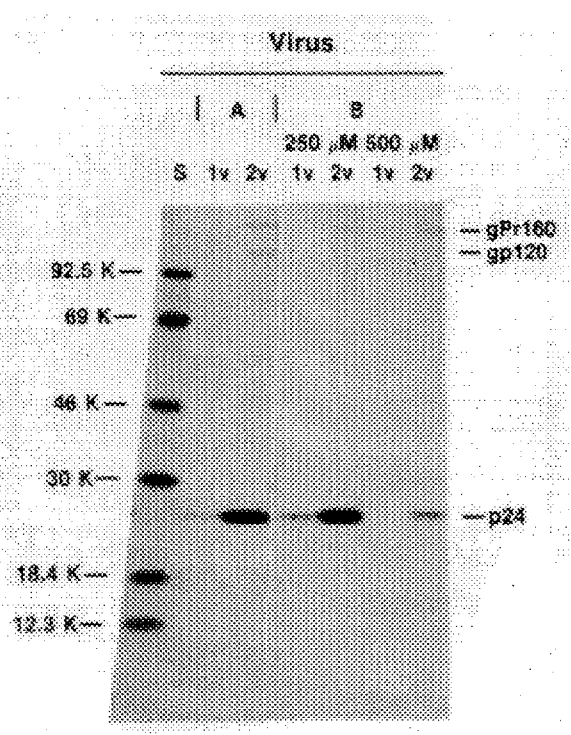

INHIBITION OF HUMAN IMMUNODEFICIENCY VIRUS-1 INFECTIVITY IN HUMAN CELLS

FIELD OF THE INVENTION

The present invention is concerned with the use of certain quinolinyl and acridinyl derivatives to inhibit the infectivity of Human Immunodeficiency Virus-1 in human cells.

BACKGROUND OF THE INVENTION

Weak bases such as chloroquine are known to cause vacuolation and swelling of intracellular acidic compartments and to raise the pH of these compartments (1,2,3,4, 5,6). Such compounds have been used to study cellular endocytic/exocytic pathways and posttranslational processing of glycoproteins (3,4,5,7,8), and have been extensively used to study the entering events of animal viruses into cells (9,10,11,12,13,14,15,16,17,18).

Studies of Stein et al (18) have shown that HIV entry into T cells by the CD4 receptor-mediated endocytosis is pH-independent and not inhibited by weak bases. The effect of weak bases, such as chloroquine on the exocytic pathways leading to the maturation and release of infectious HIV was not studied.

Tsai and Oroszlan (19) have described proteolytic processing and novel glycosylation pathways for retroviral envelope proteins and characterized the env precursor polyprotein of avian reticuleondotheliosis virus (REV-A) as being modified by unusually large sialic acid-rich complex-type carbohydrate moieties (19).

The compounds amodiaquin, chloroquine, hydroxychloroquine, primaquine and quinacrine and/or pharmaceutically acceptable salts thereof are generally known to be useful in the chemotherapy of malaria. Further, chloroquine is the most commonly used of all anti-malarial agent (20).

SUMMARY OF THE INVENTION

The present invention is concerned with methods of inhibiting the infectivity of Human Immunodeficiency Virus-1 (HIV-1) in human cells infected therewith. The present invention is further concerned with methods of inhibiting the infectivity of HIV-1 in the cells of a patient infected therewith; the patient infected with HIV-1 may additionally have Acquired Immunodeficiency Syndrome (AIDS).

Specifically, the present invention provides for the following advantageous methods.

1. A method of inhibiting HIV-1 infectivity in chronically infected human cells, the method comprising:
   contacting HIV-1 infected human cells with an effective HIV-1 replication inhibiting amount of a compound selected from the group consisting of:
   amodiaquin,
   a pharmaceutically acceptable salt of amodiaquin,
   chloroquine,
   a pharmaceutically acceptable salt of chloroquine,
   hydroxychloroquine,
   a pharmaceutically acceptable salt of hydroxychloroquine,
   quinacrine,
   a pharmaceutically acceptable salt of quinaqurine,
   primaquine, and
   a pharmaceutically acceptable salt of primaquine.

2. The method recited in paragraph 1, wherein the compound administered is chloroquine or a pharmaceutically acceptable salt thereof.

3. The method of paragraph 1, wherein said compound or pharmaceutically acceptable salt thereof is contacted with human cells in vitro.

4. The method of paragraph 1, wherein said compound or pharmaceutically acceptable salt thereof is contacted with said cells by administering said compound to a patient infected with HIV-1.

5. The method of paragraph 1, wherein the compound is contacted with said cells by administering said compound to a patient infected with HIV-1, and having AIDS.

6. A method of inhibiting HIV-1 infectivity in chronically infected human cells, the method comprising: contacting HIV-1 infected human cells with an effective HIV-1 replication amount of a compound having the formula:

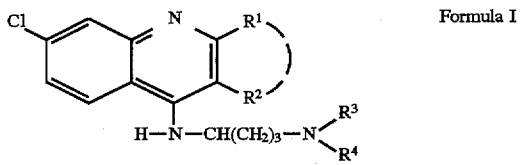

Formula I wherein
  $R^1$ and $R^2$ are each hydrogen, or join to form a cyclic structure of the formula:

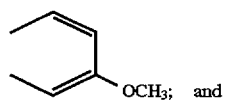

$R^3$ and $R^4$, same or different, are hydrogen, $C_1$–$C_8$ lower alkyl or hydroxy substituted $C_1$–$C_8$ lower alkyl; and the pharmaceutically acceptable salts thereof.

7. The method of paragraph 6, wherein the compound of Formula I is:
   chloroquine,
   a pharmaceutically acceptable salt of chloroquine,
   hydroxychloroquine,
   a pharmaceutically acceptable salt of hydroxychloroquine,
   quinacrine, or
   a pharmaceutically acceptable salt of quinacrine.

8. The method of paragraph 6, wherein the compound of Formula I is chloroquine or a pharmaceutically acceptable salt thereof.

9. The method of paragraph 6, wherein said compound of Formula I or a pharmaceutically acceptable salt thereof is contacted with human cells in vitro.

10. The method of paragraph 6, wherein said compound of Formula I or a pharmaceutically acceptable salt thereof is contacted with said cells by administering said compound to a patient infected with HIV-1.

11. The method of paragraph 6, wherein said compound of Formula I or a pharmaceutically acceptable salt thereof is contacted with said cells by administering said compound to a patient infected with HIV-1, and having AIDS.

The following glossary of terms is provided in order to remove any ambiguity which may exist as to the use of certain terms herein.

The term "HIV-1" as used herein means Human Immunodeficiency Virus type 1.

The term "AIDS" as used herein means Acquired Immunodeficiency Syndrome.

The term "amodiaquin" as used herein means 4-[(7-chloro-4-quinolinyl)amino]-2-[(diethylamino)methyl] phenyl. Methods of synthesis for amodiaquin are disclosed in U.S. Pat. Nos. 2,474,819 and 2,474,821, which are herein incorporated by reference.

The term "chloroquine" as used herein means $N^4$-(7-chloro-4-quinolinyl)-N',N'-diethyl-1,4-pentanediamine. Methods of synthesis for chloroquine are disclosed in U.S. Pat. No. 2,233,970, herein incorporated by reference.

The term "hydroxychloroquine" as used herein means 2-[[4-[(7-chloro-4-quinolinyl)amino]pentyl]ethylamino]-ethanol. Methods of synthesis for hydroxychloroquine are disclosed in U.S. Pat. No. 2,546,658, herein incorporated by reference.

The term "primaquine" as used herein means $N^4$-(6-methoxy-8-quinolinyl)-1,4-pentanediamine. A method for the synthesis of primaquine is disclosed by Elderfield et al in J. Am. Chem. Soc. 77, 4816 (1955), herein incorporated by reference.

The term "quinacrine" as used herein means $N^4$-(6-chloro-2-methoxy-9-acridinyl)-$N^1$,$N^1$-diethyl-1,4-pentanediamine. A method for the synthesis of quinacrine is disclosed in U.S. Pat. No. 2,113,357, herein incorporated by reference.

The term "pharmaceutically acceptable salt" as used herein includes acid addition salts, hydrates, alcoholates, and quaternary salts of the active quinolinyl and acridinyl derivatives disclosed herein, which are physiologically compatible in humans. The acid addition salts may be formed by either strong or weak acids. Representative of strong acids are hydrochloric, phosphoric and sulfuric acids. Representative of weak acids are fumaric, maleic, succinic, oxalic, citric, tartaric, hexamic and the like.

The term "$C_1$–$C_8$ lower alkyl" as used herein means lower alkyl radicals having one to eight carbon atoms. Such lower alkyl radicals include methyl, ethyl, n-propyl, i-propyl, n-butyl, i-butyl, t-butyl, amyl, isoamyl, hexyl, heptyl, octyl, isooctyl and the like.

The term "hydroxy-substituted $C_1$–$C_8$ lower alkyl" as used herein means a $C_1$–$C_8$ lower alkyl radical as defined herein, substituted by a hydroxyl group. Exemplary of such hydroxy substituted $C_1$–$C_8$ lower alkyl radicals are hydroxy methyl radical, hydroxy ethyl radical, n-propyl alcohol radical, i-propyl alcohol radical, n-amyl alcohol radical, isoamyl alcohol radical, and the like.

Figure 1:
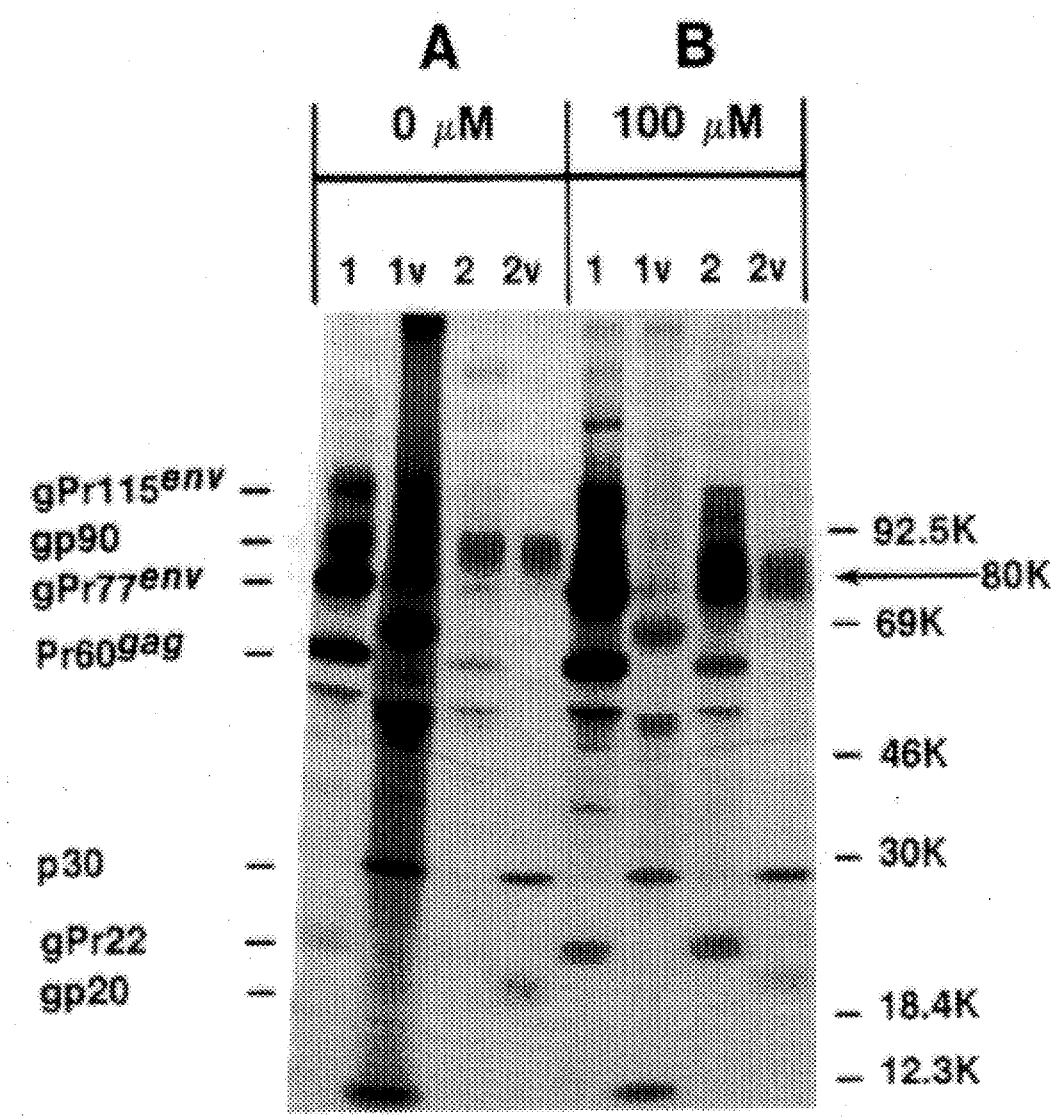
FIG. 1.

Autoradiograph showing the effects of chloroquine on the processing of REV-A env gene encoded proteins in a typical pulse-chase experiment. The autoradiograph shows the following results: Panel A, Control; Panel B, treatment with chloroquine-diphospate (100 µM); lanes 1 (cell lysates) and 1v (viruses), pulse; lanes 2 (cell lysate) and 2v (viruses) chase.

FIGS. 2a and 2b.

FIGS. 2a and 2b are autoradiographs showing the effects of chloroquine on the processing of HIV-1 gene-encoded proteins in a typical pulse-chase experiment. The autoradiographs show the following results: FIG. 2a depicts cell lysates and FIG. 2b depicts virus. Section B of FIGS. 2a and 2b showing treatment with chloroquine (250 and 500 µM); lanes 1 (cell lysate) and 1v (the virus), pulse; lanes 2 (cell lysate) and 2v (the virus), chase.

DETAILED DESCRIPTION OF THE INVENTION

The following detailed description of the present invention is divided into the following sections: Materials and Methods (utilized), Results and Discussions, Detailed Description of the Drawings, and Pharmaceutical Preparations.

Much of the discussions which follow center upon the use of chloroquine in the methods of the present invention. The same should not be considered limiting to the present invention, however, since the present invention is only to be limited by the scope of the appended claims.

1. MATERIALS AND METHODS

Cell Lines and Viruses

A chicken bone-marrow cell line persistently producing REV-A (REV/cBMC) (21) was used to study intracellular and extracellular REV-A proteins. The H9 cell line that was persistently and productively infected with HTLV-IIIB (22, 23) was used for the similar studies, and that infected with HIV-RFII (22,23), for studies of chloroquine effects on HIV infectivity. the HIV-1's were obtained from R. Gallo, and were prepared and stocked as described previously (24). The CEM-SS, a biological clone from the CEM cell line, was used for the microtiter syncytial forming assay (24,25). The cell lines, both infected and uninfected, were maintained in RPMI 1640 supplemented with heat-activated 10% fetal bovine serum, 1% L-glutamine and penicillin-streptomycin.

Antisera

The antisera raised in rabbits against various REV-A proteins were prepared and characterized as described (19, 26,27,28). The antisera to HIV p24 were obtained by immunizing rabbits with inactivated HTLV-IIIB, and those to gp120 was raised in rabbits by immunizing with HTLV-IIIB gp120 C-terminal synthetic peptides.

Metabolic Labeling of Cell Cultures and Viruses, Radioimmunoprecipitation, SDS-PAGE and Autoradiography.

The procedures utilized have been described in general previously (19) and are provided in the Detailed Description of FIGS. 1 and 2a and 2b hereinbelow.

Microtiter Syncytial Forming Assay.

The assays performed as described by Nara et al., (24,25) were used to determine the HIV infectivity, and the effects on the infectivity by chloroquine (Sigma).

Reverse Transcriptase Assay and Cell Viability.

A standard reverse transcriptase (RT) assay procedure was performed as follows. To a 10-µl sample, Triton X-100 and dithiothreitol (DTT) solutions were added to final concentrations of 0.5% Triton X-100 and 0.015% DTT before the assays were performed. Ten microliters of the samples were then mixed with 30 of magnesium cocktail and 10 of $^3$H-TTP (preparations of the solutions are described as below). The mixture was incubated at 37° C. for 30 min. Samples were harvested onto DE81 ion exchange paper (Whatman) and allowed to absorb for 15 min. The papers were soaked and washed in 5% $Na_2HPO_4$ buffer, followed by more washings with distilled water. The papers were then dried and counted. The formula for magnesium cocktail: 1M tris- HCl pH 7.8 (2 volumes), 3M KCl (1 volume), 0.3% (w/v) DTT (5 volumes), 0.1M magnesium acetate (5 volumes), poly(rA)-p(dT)$_{12-18}$ of 2 units/ml (Pharmacia) (10 volumes), distilled water (6.5 volumes) and 10% Triton X-100 (0.5 volumes); the formula for $^3$H-TTP solution: (Methyl-$^3$H)thymidine 5' triphosphate (ammonium salt) diluted in 1:5 with water before use. Each sample was run in triplicate and the results are shown in counts per ml (CPM) of each the supernatants. Each of the relative values is also shown in parentheses using the 0 µM-treatment as 100. The cell viability was determined by trypan blue dye exclusion.

2. RESULTS AND DISCUSSIONS

First, we present our studies of the effect of chloroquine on the glycosylation pathways and the maturation of REV-A envelope glycoprotein. In a typical pulse-chase experiment, REV-A-producing chicken bone marrow cells (REV/cBMC) (21) grown in suspension culture were labeled with [$^{35}$S] Cysteine in the presence and absence of chloroquine. Cells and extracellular virus were harvested after the pulse as well as the chase, and then lysed (see Detailed Description of FIG. 1 below). Radiolabeled proteins were precipitated with a mixture of previously individually characterized monospecific antibodies to REV-A capsid protein (p30), transmembrane protein (gp20) and surface glycoprotein (gp90) (19,26,27,28) and analyzed by SDS-gel electrophoresis followed by autoradiography. The results are shown in FIG. 1. The patterns from the culture grown in the absence of chloroquine (Panel A) are consistent with our previous findings (19) showing that $gPr77^{env}$ is the high-mannose type primary envelope precursor and $gPr115^{env}$ is the complex-type secondary precursor, which is processed in the Golgi network into the mature gp90 (complex type) and gp22 (high-mannose type), the intermediate precursor to gp20 of the mature virion. Treatment of cells with 100 μM chloroquine (Panel B) resulted in a substantial reduction of the molecular size of the sialic acid-rich complex-type glycoproteins, both the precursor, $gPr115^{env}$ and gp90. This is clearly seen after the chase (lanes B2 and B2v). The observed ≈10 kilodalton (kD) size reduction (see band labeled 80K in lane B2v) is nearly equivalent to the total size of the three terminal sialoligosaccharide chains (≈4 kD each) found in the three N-linked complex carbohydrate moieties of gp90 (19).

To determine whether chloroquine exerts any effect on HIV-1 glycoproteins, immunoprecipitation experiments were performed using H9 cells chronically infected with the HTLV-IIIB strain (22,23) of HIV-1 and a mixture of antibodies specifically recognizing gp120 and p24. The results are shown in FIGS. 2a and 2b (FIG. 2a for cell lysates and FIG. 2b for the virus). In the presence of 250 μM chloroquine, the cellular gp120 after the 3.5-hour chase appears to be only slightly reduced in size (left panel, lane B2, compared with lane B1 of the 90-min pulse or with lanes A1 and A2 of the control), but its incorporation into the extracellular virion was apparently retarded. Note the presence of gp120 in lane A2V, left panel (control) and its nearly complete absence in lane B2v, right panel. As suggested from the REV-A study and will be discussed further later, the size reduction of HIV-1 gp120 may also be due to the effect of chloroquine on terminal sialylation. The minor size reduction of gp120 relative to the much greater effect on REV-A gp90 is consistent with recent findings from biochemical studies (29,30) showing that terminally sialylated complex-type oligosaccharides of gp120 contain only one or two neuraminic acid residues per chain in contrast to REV-A gp90 containing unusually large terminal polysialic acid chains (19). When the cells were treated with chloroquine at a higher concentration (500 μM), the effects were similar to those with 250 μM, but at the higher concentration less incorporation of the label into proteins was observed, probably due to cell toxicity and inhibition of protein synthesis. We have determined the effects of primaquine are similar to those found with chloroquine.

Based upon the above findings, we believe it fully expectable that all the compounds encompassed by the paragraphs numbered 1 and 6 above, would produce results similar to those obtained with chloroquine and primaquine in the above test procedure.

We also studied the effect of chloroquine on the infectivity of HIV-1. H9 cells infected with HIV-1 RFII (22,23) were first treated with chloroquine at various concentrations for 45 to 60 min and then washed. Treatment with the drug in fresh medium was resumed for 4 hours. The cell-free supernatants were then collected to determine the virus titers by infectivity assays. A microtiter syncytial-forming assay with cloned CEM cells (CEM-SS) as indicator cells was used to measure syncytial-forming units (SFU) as described previously (24,25). The supernatants were also tested for reverse transcriptase (RT) activity. Cell viability was determined by trypan blue exclusion. The results of two independent experiments are shown in Table 1, below. For virus produced in the presence of 100 μM chloroquine, the number of SFUs was reduced to about 50% of the untreated. Increasing the drug concentration in the medium resulted in substantially greater inhibition. At the highest concentration of chloroquine used (300 μM), virus infectivity was inhibited by 84% in the first and 76% in the second experiment. The reductions were not due to cell death, since cell viability was apparently not affected at these concentrations (Table 1). Nor were the reductions due to the effect of the drug on the indicator cells during the virus adsorption period. Titration of supernatants collected from the control cells grown without chloroquine to which the drug was added (300 μM) before serial dilutions did not show significant reduction of SFUs as compared to the control and shown by data of Table 1 (see lines 0 μM(+)).

TABLE I

Effects on the syncytial formation and reverse transcriptase activity of human immunodeficiency viruses produced by infected cells treated with chloroquine Experiment 1

| Cloroquine | SFU/ml | RT(CPM ×) 103/ml) | Cell Viability % |
|---|---|---|---|
| 0 μM | 76,230 (100%) | 806 (100) | 91.2 |
| 100 μM | 41,220 (54.1) | 762 (94.4) | 89.2 |
| 200 μM | 38,430 (50.4) | 607 (75.1) | 95.7 |
| 300 μM | 20,460 (23.8) | 447 (55.3) | 91.4 |
| 0 μM(+) | 69,660 (91.4) | 992 (122.8) | — |

Experiment 2

| Cloroquine | SFU/ml | RT(CPM ×) $10^3$/ml) | Cell Viability % |
|---|---|---|---|
| 0 μM | 72,540 (100) | 404 (100) | 90.3 |
| 100 μM | 33,656 (46.4) | 303 (77.2) | 89.8 |
| 200 μM | 19,420 (26.8) | 223 (53.5) | 90.5 |
| 300 μM | 11,400 (15.7) | 158 (41.1) | 86.3 |
| 0 μM(+) | 68,940 (95.0) | 334 (84.8) | — |

Note:

* Quantitative microtiter syncytial-forming assay (SFA) developed by Nara et al (24,25) was used to measure syncytial-forming units (SFU). Briefly, the infected cells (RFII/H9) growing in active phase in complete RPMI 1640 were washed and then treated with the drugs of various concentrations for 46 to 60 min. The treated cells were washed again and retreated with the drugs in the complete media, respectively, in the same concentrations as for the pretreatments for additional 4 hours. The cells were then incubated at 37° C., 5% $CO_2$. Two milliliters (2 ml) of cells (about 5 to 10×10$^5$ cells/ml) were used for each treatment. The cells without the drugs served as the controls. After incubations, 1 ml of cell suspension from each of the treatments was centrifuged and cell-free supernatants were used for SFA and the RT assay. The remaining 1 ml of cell suspensions was used to examine the cells for viability. The supernatants, undiluted and diluted at 1:3, 1:9 and 1:18, were used for SFA. For the controls, the supernatants were divided into two portions. One portion was diluted as above and indicated as the 0 μM treatments to serve as the controls without the drugs. To the other portion, the drugs were added to a concentration of 300 μM followed by dilutions as above, and the samples were indicated as the 0 μM(+) treatments to serve as the control for the drug effect on the CEM-SS cells during the virus adsorption period. Each of the dilutions was run in duplicate in complete media and a 50-μl sample from each was mixed with an equal volume ($50 \times 10^3$ cells) of CEM-SS cells for SFA. The mixtures were then placed in 96-well tissue culture plates pretreated with poly-L-lysine and incubated at 37° C., 5% $CO_2$, for 60 min. The supernatants were then removed and 210 μl of complete media was replaced in each well. After a 3-day incubation, the SFUs were counted. The means of SFUs of the duplicate samples from each of the dilutions in the range of 10 to 250 SFUs per well were taken to estimate SFUs per ml of supernatants, and the means from two different dilutions were used to estimate the means of SFU/ml for each of treatments as shown in the Table. Each relative value of SFU/ml is shown in parentheses as percentage on the basis of the 0 μM treatments as 100.

As a comparison to results obtained with the active compounds of the present invention, we note McClure et al. (16) showed that a treatment of HIV-infected T cells with $NH_4Cl$ (30 mM) for 18 hours resulted in 95% reduction in the production of infectious virus and 10 to 15% cell death. This is similar to the observed reduction of infectivity with chloroquine in our experiments. With chloroquine treatments, as can be seen in Table I, the RT activity was reduced in the two separate experiments to about 90 to 94%, 54 to 75% and 41 to 55%, at 100 μM, 200 μM and 300 μM, respectively (Table 1). The drug did not affect the RT assay itself (see Footnote to Table 1). The reduction in the RT activity is likely due to the decrease in the number of virions produced. However, the extent of reduction of RT was apparently less than that of infectivity (Table 1).

N-linked carbohydrate structures of HIV gp120 were found by biochemical studies to be of unique diversity containing high-mannose type, hybrid type, and four categories of complex-type chains, with or without N-acetyl-lactosamine repeats and a core-region fucose residue (29, 30). The functional roles of carbohydrates were studied by various approaches including the use of glycosidases (31, 32, 33, 34) and lectins (35, 36). The effects of glycosylation inhibitors that block trimming enzymes functioning in the early stages of the glycosylation pathways were also studied (31, 36, 37, 38, 39, 40, 41, 42). Chloroquine is known to raise the acidic milieu of the Golgi apparatus (1, 3, 4, 5), and to affect the proteolytic processing of secretory proteins that occur in these compartments (7, 8). Furthermore, as shown in the experiments with REV-A, chloroquine appears to inhibit sialylation of REV-A gp90 that likely occurs in the trans-Golgi networks (19) with which sialyltransferases are associated in certain cell types (4, 43). Studies with monension showed that this drug reduced HIV infectivity and syncytial formation (44, 45), likely by blocking sialylation and partially affecting the addition of galactose and fucose (44). Treatment of HIV with neuramimidase reduced its infectivity as well as the size of gp120 (34). These results support that terminal glycoglyation of gp120 may play a crucial role for HIV infectivity. Chloroquine may also inhibit cleavage of gp160 (see FIG. 1). However, the exact mechanisms by which chloroquine inhibits HIV infectivity has yet to be determined by direct analysis of HIV gp120/160 from chloroquine-treated cells. From our studies chloroquine appeared to be an effective inhibitor of HIV-1 by reducing both the yield and infectivity of the virus produced in chronically infected cells. However, 100% inhibition was not obtained even at the highest concentration of chloroquine used. A likely explanation may be the relatively short exposure (45 to 60 min) to chloroquine prior to the start of collecting extracellular virus. Thus, normal infectious particles formed prior to treatment may have been present at low levels in the virus stocks we assayed.

Based upon the above results obtained with chloroquine contained in Table I, it is thought expectable that each of the active compounds encompassed by paragraph numbers 1 and 6 in the Summary of the Invention above, will be active in inhibiting the infectivity of HIV-1, in vivo or in vitro, when contacted with human cells infected with HIV.

3. DETAILED DESCRIPTION OF THE DRAWINGS

FIG. 1. Effects of chloroquine on the processing of REV-A env gene-encoded proteins. REV/cBMC was grown in RPMI 1640 supplemented with 10% heat-inactivated fetal bovine serum (FBS), 1% L-glutamine and 1% penicillin-streptomycin. For drug treatments, the actively growing cells (~106 cells/ml) were clarified by centrifugation and resuspended at a density of $10^7$ cells/ml in cysteine-free RPMI 1640 plus 10% dialyzed FBS, 1% L-glutamine, and antibiotics. A stock solution of the drug was added to a 10-ml cell suspension followed by labeling with [$^{35}$S]cysteine (30 μCi/ml) for 60 min of incubation in 5% $CO_2$ at 37° C. At the end of the incubation, the cell suspension was equally divided into two tubes and then clarified and washed by centrifugation at 500 to 1000 rpm for 5 min using an IEC HN-S centrifuge (Damon/IEC Division). After washing, one tube of the sample was then disrupted with 0.5 ml of lysing buffer [LB: 0.02M tris-HCl pH 7.5, 0.05M NaCl, 0.5% sodium deoxycholate, 0.5% NP40, plus aprotinin (10 μg/ml) and phenylmethylsulfonyl fluoride (PMSF, 1 mM)]. Cell lysates were clarified at 15,000 rpm (Eppendorf microcentrifuge 5415) for 10 to 30 min. The virus was harvested by pelleting from clarified culture media using centrifugation at 40,000 rpm (Beckman L3-50 ultracentrifuge) for 90 min in nitrocellulose tubes that were cushioned at the bottom with 20% sucrose in TNE buffer (10 mM tris-HCl pH 7.0, 0.1M NaCl, 0.001M EDTA). The virus pellets were then solubilized with 100 μl of LB. The other tube of the sample was resuspended in 10 ml of the complete medium and the incubation was resumed for an additional 150 min in the presence of the drug with the same concentration as for the labeling. At the end of the chase, cell lysates were obtained and viruses were harvested and solubilized as described above. The samples for the control were treated similarly without drugs. To perform immunoprecipitations, 10% of the samples was used. The samples were reacted with a mixture of antibodies to REV-A gp20, gp90 peptide and p30 (19,26,27,28) in the presence of protein A Sepharose at 4° C. overnight. The immunoprecipitates were washed and subjected to SDS-gel electrophoresis on a 7.5 to 18% gradient. The gels were dried and autoradiographs were developed from the gels. A stock solution of 0.1M for chloroquine-diphosphate (Sigma) was prepared in double-distilled sterile water. The pH of the solutions that were diluted to the final concentrations with media were about 7.1 to 7.35. The autoradiograph made from an overnight exposure shows the following results: Panel A, control; Panel B, treatment with chloroquine-diphosphate (100 μM). Lanes 1 (cell lysates) and 1ν (viruses), pulse; lanes 2 (cell lysates) and 2ν (viruses), chase.

FIGS. 2a and 2b. Effects of chloroquine on the processing of HIV-1 gene-encoded proteins. H9 cells chronically infected with HIV IIIB (HIV-IIIB/ H9) were grown in the medium that was used for REV/cBMC (FIG. 1). The cultures were diluted and replenished with fresh H9 culture three days before the drug experiments were performed. The procedures that involved the treatment of the drugs to the development of autoradiographs are similar to those described for REV/cBMC except for the following modifications. The actively growing cells at $2\times10^5$ cells/ml were resuspended to a density of $20\times10^5$ cells/ml in cysteine/methionine-free medium plus 10% virus-free conditioned medium (VFCM), which was also included in the media that was used in the next steps. The cells (10 ml) were treated with drugs for 60 min followed by labeling with [$^{35}$S] cysteine/[$^{35}$S]methionine (15 μCi each/ml) for 90 min (except the control, which ran for 60 min). One half of the labeled culture (5 ml) was diluted to 10 ml followed by the chase for 3.5 hours. For immunoprecipitation, $\frac{1}{15}$ of the cell lysate (100 μl ) and 40 μl of the solubilized virus (equivalent to the amount produced by $4\times10^5$ cells) were used for each treatment. The cell lysates contained about 2.7 to $6.8\times10^6$ counts per minute (CPM) with the exception that B2 (500 μM) were in the range of 0.3 to $1.5\times10^6$ CPM; the solubilized viruses contained 0.10 to $0.21\times10^6$ CPM. A mixture of two antisera was used: Antiserum to gp120, which was raised in rabbits by immunizing with HTLV-IIIB gp120 C-terminal synthetic peptide, and was shown to recognize gp120 and gp160; p24 antibodies, which was obtained by immunizing rabbits with inactivated HTLV-IIIB and was shown to precipitate p24 and Pr55. The results are shown in the autoradiographs: FIG. 2a depicts cell lysates; FIG. 2b virus. Section A, control; Section B, treatment with chloroquine (250 and 500 μM). Lanes 1 (cell lysate) and 1ν (the virus), pulse; lanes 2 (cell lysate) and 2ν (the virus), chase.

4. PHARMACEUTICAL COMPOSITIONS

When the methods herein disclosed include administering one of the active compounds of the present invention to a patient infected with HIV-1, they are best carried out by administering the active ingredients in a pharmaceutical composition containing at least one of the active compounds in association with a pharmaceutical carrier or excipient. The active compounds, thus presented in a therapeutic composition, are suitable for oral, rectal or parenteral administration to a patient infected with HIV-1. Thus, for example, a composition for oral administration can take the form of elixirs, capsules, tables, or coated tablets containing carriers conveniently used in the pharmaceutical art. Suitable tableting excipients include lactose, potato, and maize starches, talc, gelatin, stearic and silicic acids, magnesium stearate and polyvinyl pyrrolidone.

For parenteral administration, the carrier can be comprised of a sterile parenterally acceptable liquid; e.g., water or arachis oil contained in ampoules.

In compositions for rectal administration, the carrier can be comprised of a suppository base; e.g., cocoa butter or glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be consistent with the dosage form employed. The exact individual dosages as well as daily dosages will, of course, be determined according to standard medical principles under the direction of a physician.

It is generally thought that when the active compounds herein disclosed are administered to a patient in the methods of the present invention, they generally should be administered orally, but that parenteral or rectal administration can be valuable in instances, where oral administration is not readily feasible. When the active compounds of the present invention are administered orally to inhibit the infectivity of HIV-1 in a patient, it is thought one should administer an effective amount which is about $\leq 10$ mg/kg/day to said patient, and preferably that one should administer an effective amount which is about $\leq 5$ mg/kg/day to said patient.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The scope of the present invention is only limited by the scope of the appended claims.

REFERENCES

1. Anderson R. G. W., and Orci L.: A view of acidic intracellular compartments. J Cell Biol 1988;106:539–543.
2. Dean R. T., Jessup W., and Roberts C. R.: Effects of exogenous amines on mammalian cells, with particular reference to membrane flow. Biochem J 1984;217:27–40.
3. de Duve C., de Barsy T., Poole B., Trouet A., Tulkens P., and van Hoof F.: Lysosomotropic agents. Biochem Pharmacol 1974;23:2495–2531.
4. Griffiths G., and Simons K.: The trans Golgi network: sorting at the exit site of the Golgi complex. Science 1986;234:438–443.
5. Krogstad D. J., and Schlesinger P. H.: Acid-vesicle function intra-cellular pathogens, and the action of chloroquine against *plasmodium falciparum*. N Engl J Med 1987;317:542–549.
6. Mellman I., Fuchs R., and Helenius A.: Acidification of the endocytic and exocytic pathways. Ann Rev Biochem 1986;55:663–700.
7. Oda K., and Ikehara Y.: Weakly basic amines inhibit the proteolytic conversion and proalbumin to serum albumin in cultured rat hepatocytes. Eur J Biochem 1985;52:605–609.
8. Oda K., Koriyama Y., Yamada E., Ikehara Y.: Effects of weakly basic amines on proteolytic processing and terminal glycosylation of secretory proteins in cultured rat hepatocytes. Biochem J 1986;240:739–745.
9. Andersen K. B., and Nexo B. A.: Entry of murine retrovirus into mouse fibroblasts. Virology 1983;125:85–98.
10. Carrillo E. C., Giachetti C., and Campos R.: Early steps in FMDV replication: Further analysis on the effects of chloroquine. Virology 1985;147:118–125.
11. Helenius A., Marsh M., and White J.: Inhibition of Semliki Forest virus penetration by lysosomotropic weak bases. J Gen Virol 1982;58:47–61.
12. Maddon P. J., Dalgleish A. G., McDougal J. S., Clapham P. R., Weiss R. A., and Axel R.: The T4 gene encodes the AIDS virus receptor and is expressed in the immune system and the brain. Cell 1986;47:333–348.

13. Madshus I. H., Olsnes S., and Sandvig K.: Mechanism of entry into the cytosol of poliovirus Type 1: Requirement of low pH. J Cell Biol 1984;98:1194–1200.

14. Marsh M.: The entry of enveloped viruses into cells by endocytosis. Biochem J 1984;218:1–10.

15. Marsh M., and Dalgleish A.: How do human immunodeficiency viruses enter cells? Immunology Today 1987;8:369–371.

16. McClure M. O., Marsh M., and Weiss R. A.: Human immunodeficiency virus infection of CD4-bearing cells occurs by a pH-independent mechanism. EMBO J 1988;7:513–518.

17. Redmond S., Peters G., and Dickson C.: Mouse mammary tumor virus can mediate cell fusion at reduced pH. Virology 1984;133:393–402.

18. Stein B. S., Gowda S. D., Lifson J. D., Penhallow R. C., Gensch K. G., and Engleman E. G.: pH-independent HIV entry into CD4-positive T cells via virus envelope fusion to the plasma membrane. Cell 1987;49:659–668.

19. Tsai W.-P., and Oroszlan S.: Novel glycosylation pathways of retroviral envelope proteins identified with avian reticuloendotheliosis virus. J Virol 1988;62:3167–3174.

20. Goodman A. G., Gilman L. S., Rall T. W., and Murad F.: The pharmacological basis of therapeutics, 7th ed. Macmillan, New York, 1985, pp. 1029–1048.

21. Hoelzer J. D., Franklin R. B., and Bose Jr. H. R.: Transformation by reticuloendotheliosis virus: Development of a focus assay and isolation of a nontransforming virus. Virology 1979;93:20–30.

22. Popovic M., Sarngadharan M. G., Read E., Gallo R. C.: Detection, isolation, and continuous production of cytopathic retroviruses (HTLV-III) from patients with AIDS and Pre-AIDS. Science 1984;224:497–500.

23. Starcich B. R., Hahn B. H., Shaw G. M., McNeely P. D., Modrow S., Wolf H., Parks E. S., Parks W. P., Josephs S. F., Gallo R. C., and Wong-Staal F.: Identification and characterization of conserved and variable regions in the envelope gene of HTLV-III/LAV, the retrovirus of AIDS. Cell 1986; 45:637–648.

24. Nara P. L., Hatch W. C., Dunlop N. M., Robey W. G., Arthur L. O., Gonda M. A., and Fischinger P. J.: Simple, rapid, quantitative, syncytium-forming microassay for the detection of human immunodeficiency virus neutralizing antibody. AIDS Res and Human Retroviruses 1987;3:283–302.

25. Nara P. L., and Fischinger P. J.: Quantitative infectivity assay for HIV-1 and -2. Nature 1988;332:469–470.

26. Tsai W. -P., and Oroszlan S.: Site-directed cytotoxic antibody against the C-terminal segment of the surface glycoprotein gp90 of avian reticuloendotheliosis virus. Virology 1988;166:608–611.

27. Tsai W. -P., Copeland T. D., and Oroszlan S.: Purification and chemical characterization of avian reticuloendotheliosis virus gag-gene-encoded structural proteins. Virology 1985;140:289–312.

28. Tsai W. -P., Copeland T. D., and Oroszlan S.: Biosynthesis and chemical and immunological characterization of avian reticuloendotheliosis virus env gene-encoded proteins. Virology 1986;155:567–583.

29. Geyer H., Holschbach C., Hunsmann G., Schneider J.: Carbohydrates of human immunodeficiency virus: Structure of oligosaccharides linked to the envelope glycoprotein 120. J Biol Chem 1988;263:11760–11767.

30. Mizuochi T., Spellman M. W., Larkin M., Solomon J., Basa L., and Feizi T.: Carbohydrate structures of the human-immunodeficiency-virus (HIV) recombinant envelope glycoprotein gp120 produced in Chinese-hamster ovary cells. Biochem J 1988;254:599–603.

31. Fennie C. and Lasky L. A.: Model for intracellular folding of the human immunodeficiency virus type 1 gp120. J Virol 1989;63:639–646.

32. Fenouillet E., Clerget-Raslain B., Gluckman J. C., Guétard D., Montagnier L., and Bahraoui E.: Role of N-linked glycans in the interaction between the envelope glycoprotein of human immunodeficiency virus and its CD4 cellular receptor. Structural enzymatic analysis. J Exp Med 1989;169:807–822.

33. Matthews T. J., Weinhold K. J., Lyerly H. K., Langlois A. J., Wigzell H., and Bolognesi D. P.: Interaction between the human T-cell lymphotropic virus type $III_B$ envelope glycoprotein gp120 and the surface antigen CD4: Role of carbohydrate in binding and cell fusion. Proc Natl Acad Sci USA 1987;84:5424–5428.

34. McDougal J. S., Nicholson J. K. A., Cross G. D., Cort S. P., Kennedy M. S., and Mawle A. C.: Binding of the human retrovirus HTLV-III/LAV/ARV/HIV to the CD4 (T4) molecule: Conformation dependence, epitope mapping, antibody inhibition, and potential for idiotypic mimicry. J Immunol 1986;137:2937–2944.

35. Lifson J., Coutré S., Huang E., and Engleman E.: Role of envelope glycoprotein carbohydrate in human immunodeficiency virus (HIV) infectivity and virus-induced cell fusion. J Exp Med 1986;164:2101–2106.

36. Robinson W. E. Jr., Montefiori D. C., and Mitchell W. M.: Evidence that mannosyl residues are involved in human immunodeficiency virus type 1 (HIV-1) pathogenesis. AIDS Res Human Retrovir 1987;3:265–282.

37. Gruters R. A., Neefjes J. J., Tersmette M., de Goede R. E. Y., Tulp A., Huisman H. G., Miedema F., and Ploegh H. L.: Interference with HIV-induced syncytium formation and viral infectivity by inhibitors of trimming glucosidase. Nature (London) 1987;330:74–77.

38. Montefiori D. C., Robinson W. E. Jr., and Mitchell W. M.: Role of protein N-glycosylation in pathogenesis of human immunodeficiency virus type 1. Proc Natl Acad Sci USA 1988;85:9248–9252.

39. Pal R., Hoke G. M., and Sarngadharan M. G.: Role of oligosaccharides in the processing and maturation of envelope glycoproteins of human immunodeficiency virus type 1. Proc Natl Acad Sci USA 1989;86:3384–3388.

40. Walker B. D., Kowalski M., Goh W. C., Kozarsky K., Krieger M., Rosen C., Rohrschneider L., Haseltine W. A., and Sodroski J.: Inhibition of human immunodeficiency virus syncytium formation and virus replication by castanospermine. Proc Natl Acad Sci USA 1987;84:8120–8124.

41. Elbein A. D.: Inhibitors of the biosynthesis and processing of N-linked oligosaccharide chains. Ann Rev Biochem 1987;56:497–534.

42. Kornfeld R. and Kornfeld S.: Assembly of asparagine-linked oligosaccharides. Ann Rev Biochem 1985;54:631–640.

43. Snider M., and Rogers O.: Membrane traffic in animal cells: cellular glycoproteins return to the site of Golgi mannosidase I. J Cell Biol 1986;103:265–276.

44. Dewar R. L., Vasudevachari M. B., Natarajan V., and Salzman N. P.: Biosynthesis and processing of human immunodeficiency virus type 1 envelope glycoproteins:

effects of monensin on glycosylation and transport. J Virol 1989;63:2452–2456.

45. Pal R., Gallo R. C., and Sarngadharan M. G.: Processing of the structural proteins of human immunodeficiency virus type 1 in the presence of monensin and cerulenin. Proc Natl Acad Sci USA 1988;85:9283–9286.

What is claimed is:

1. A method of inhibiting HIV-1 infectivity in chronically infected human cells, the method comprising:

contacting HIV-1 infected human cells with an effective HIV-1 replication inhibiting amount of chloroquine or a pharmaceutically acceptable salt thereof.

2. The method of claim 1, wherein said compound or pharmaceutically acceptable salt thereof is contacted with human cells in vitro.

3. The method of claim 1, wherein said compound or pharmaceutically acceptable salt thereof is contacted with said cells by administering said compound to a patient infected with HIV-1.

4. The method of claim 1, wherein the compound is contacted with said cells by administering said compound to a patient infected with HIV-1, and having AIDS.

* * * * *